(12) United States Patent
Holtwick et al.

(10) Patent No.: US 9,962,500 B2
(45) Date of Patent: May 8, 2018

(54) CONNECTION FOR MEDICAL DEVICE

(75) Inventors: Marc Holtwick, Frankfurt am Main (DE); Jeffrey Zajac, Franklin, MA (US); James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days. days.

(21) Appl. No.: 14/113,987

(22) PCT Filed: Apr. 26, 2012

(86) PCT No.: PCT/EP2012/057695
§ 371 (c)(1),
(2), (4) Date: Oct. 25, 2013

(87) PCT Pub. No.: WO2012/146679
PCT Pub. Date: Nov. 1, 2012

(65) Prior Publication Data
US 2014/0052077 A1  Feb. 20, 2014

Related U.S. Application Data

(60) Provisional application No. 61/480,063, filed on Apr. 28, 2011.

(30) Foreign Application Priority Data

Jul. 8, 2011   (EP) .................................... 11173282

(51) Int. Cl.
*A61M 5/34* (2006.01)
*A61M 5/158* (2006.01)

(52) U.S. Cl.
CPC ............ *A61M 5/349* (2013.01); *A61M 5/158* (2013.01); *A61M 5/34* (2013.01); *A61M 5/343* (2013.01)

(58) Field of Classification Search
CPC .......... A61M 5/32; A61M 5/349; A61M 5/34; A61M 2005/3107; A61M 2005/3103; A61M 2005/3109
(Continued)

(56) References Cited

U.S. PATENT DOCUMENTS 533,575 A    2/1895  Wilkens
2,701,566 A  *  2/1955  Krug ............................ 604/154
(Continued)

FOREIGN PATENT DOCUMENTS

CN    87105155 A    1/1988
CN    1077112 A    10/1993
(Continued)

OTHER PUBLICATIONS

English Translation of Third Office Action Issued in Chinese Patent Application No. 201280029957.8 dated May 20, 2016.

*Primary Examiner* — Imani Hayman
*Assistant Examiner* — Matthew A Engel
(74) *Attorney, Agent, or Firm* — McDonnell Boehnen Hulbert & Berghoff LLP

(57) ABSTRACT

The invention faces the technical problem of providing a tight connection between a tube and an dispense interface, while at the same time the biocompatibility of the connection can be improved. The technical problem is solved by an apparatus comprising a tube configured to guide a medium and a dispense interface. The tube comprises a first opening and a second opening, while the dispense interface comprises a recess. The recess has a first opening and a second opening and the tube is at least in part inserted into the (Continued)

recess. The tube is permanently affixed to the dispense interface by a combination of an interference fit and an adhesive, such that the interference fit prevents the adhesive from contaminating the medium.

9 Claims, 14 Drawing Sheets

(58) Field of Classification Search
USPC .................................................. 604/110, 195
See application file for complete search history.

(56) References Cited

U.S. PATENT DOCUMENTS

| | | | |
|---|---|---|---|
| 3,247,850 | A | 4/1966 | Gettig et al. |
| 3,324,854 | A * | 6/1967 | Weese ........................... 604/115 |
| 3,472,227 | A * | 10/1969 | Burke ........................... 604/243 |
| 3,523,531 | A * | 8/1970 | Burke ........................... 604/272 |
| 3,523,532 | A * | 8/1970 | Burke ........................... 604/240 |
| 3,556,099 | A * | 1/1971 | Knight et al. ................. 604/232 |
| 3,756,235 | A * | 9/1973 | Burke et al. .................. 604/240 |
| 3,903,887 | A * | 9/1975 | Antoshkiw .................... 604/272 |
| 4,240,433 | A * | 12/1980 | Bordow ........................ 604/540 |
| 4,568,346 | A * | 2/1986 | van Dijk ....................... 604/414 |
| 4,689,042 | A * | 8/1987 | Sarnoff ............... A61M 5/2066 604/136 |
| 4,795,445 | A * | 1/1989 | Jensen ........................... 604/240 |
| 4,958,625 | A * | 9/1990 | Bates et al. ................... 600/567 |
| 4,966,589 | A * | 10/1990 | Kaufman ....................... 604/174 |
| 4,968,302 | A | 11/1990 | Schluter et al. |
| 5,108,378 | A * | 4/1992 | Firth et al. .................... 604/192 |
| 5,147,323 | A * | 9/1992 | Haber ..................... A61M 5/19 604/191 |
| 5,171,214 | A * | 12/1992 | Kolber et al. ................... 604/82 |
| 5,226,895 | A | 7/1993 | Harris |
| 5,240,146 | A * | 8/1993 | Smedley ................. A61M 5/19 222/137 |
| 5,250,037 | A * | 10/1993 | Bitdinger ...................... 604/192 |
| 5,271,527 | A * | 12/1993 | Haber ..................... A61M 5/19 222/137 |
| 5,279,586 | A | 1/1994 | Balkwill |
| 5,298,023 | A * | 3/1994 | Haber ..................... A61M 5/19 604/191 |
| 5,304,152 | A | 4/1994 | Sams |
| 5,314,412 | A * | 5/1994 | Rex ......................... A61M 5/19 222/137 |
| 5,320,609 | A | 6/1994 | Haber et al. |
| 5,329,976 | A | 7/1994 | Haber et al. |
| 5,364,362 | A * | 11/1994 | Schulz .......................... 604/115 |
| 5,383,865 | A | 1/1995 | Michel |
| 5,393,497 | A * | 2/1995 | Haber .................... A61J 1/2089 137/68.11 |
| 5,478,323 | A * | 12/1995 | Westwood ............. A61M 5/19 604/191 |
| 5,478,337 | A | 12/1995 | Okamoto et al. |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 5,976,102 | A * | 11/1999 | Epstein ........................... 604/35 |
| 5,984,890 | A * | 11/1999 | Gast et al. ...................... 604/60 |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,503,229 | B2 * | 1/2003 | King ............................. 604/263 |
| 6,569,123 | B2 * | 5/2003 | Alchas et al. ................. 604/192 |
| 6,607,509 | B2 * | 8/2003 | Bobroff et al. ............... 604/136 |
| 6,666,844 | B1 * | 12/2003 | Igo et al. ...................... 604/115 |
| 6,776,776 | B2 * | 8/2004 | Alchas et al. ................. 604/198 |
| 6,899,698 | B2 | 5/2005 | Sams |
| 6,936,032 | B1 | 8/2005 | Bush, Jr. et al. |
| 6,939,322 | B2 * | 9/2005 | Crank et al. .................. 604/117 |
| 7,052,483 | B2 * | 5/2006 | Wojcik .......................... 604/162 |
| 7,241,278 | B2 | 7/2007 | Moller |
| 7,438,703 | B2 * | 10/2008 | Barrus et al. ................. 604/192 |
| 7,794,445 | B2 * | 9/2010 | Dalton ........................... 604/506 |
| 8,221,452 | B2 * | 7/2012 | Edwards ........... A61B 17/00491 604/82 |
| 8,556,861 | B2 * | 10/2013 | Tsals ............................ 604/187 |
| 2001/0056265 | A1 * | 12/2001 | Heinz et al. .................. 604/227 |
| 2002/0052578 | A1 | 5/2002 | Moller |
| 2002/0077599 | A1 * | 6/2002 | Wojcik .......................... 604/162 |
| 2002/0120235 | A1 | 8/2002 | Enggaard |
| 2003/0050609 | A1 | 3/2003 | Sams |
| 2004/0059299 | A1 | 3/2004 | Moller |
| 2004/0147901 | A1 * | 7/2004 | Py et al. ........................ 604/506 |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2009/0082732 | A1 * | 3/2009 | Hillman ................... 604/164.08 |
| 2009/0275916 | A1 | 11/2009 | Harms et al. |
| 2010/0137831 | A1 * | 6/2010 | Tsals ............................. 604/506 |
| 2011/0224609 | A1 * | 9/2011 | Tsals et al. .................... 604/117 |

FOREIGN PATENT DOCUMENTS

| | | |
|---|---|---|
| CN | 1081360 A | 2/1994 |
| EP | 0937471 A2 | 8/1999 |
| EP | 0937476 A2 | 8/1999 |
| FR | 2510892 A1 | 2/1983 |
| GB | 1215435 | 12/1970 |
| WO | 9311709 A1 | 6/1993 |
| WO | 9938554 A1 | 8/1999 |
| WO | 0110484 A1 | 2/2001 |
| WO | 2005025641 A2 | 3/2005 |

* cited by examiner

CONNECTION FOR MEDICAL DEVICE

CROSS REFERENCE TO RELATED APPLICATIONS

The present application is a U.S. National Phase Application pursuant to 35 U.S.C. § 371 of International Application No. PCT/EP2012/057695 filed Apr. 26, 2012, which claims priority to U.S. Provisional Patent Application No. 61/480,063, filed Apr. 28, 2011 and European Patent Application No. 11173282.2 filed Jul. 8, 2011. The entire disclosure contents of these applications are herewith incorporated by reference into the present application.

FIELD OF INVENTION

The present patent application relates to medical devices for delivering at least one drug agent from a reservoir, in particular at least two drug agents from separate reservoirs. Such drug agents may comprise a first and a second medicament. The medical device includes a dose setting mechanism for delivering the drug agents automatically or manually by the user. The invention relates in particular to the connection of a tube of a medical device to other parts of a medical device.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.
2. Attach a dose dispenser, such as a double-ended needle assembly, to a distal end of the dispense interface. In this manner, a proximal end of the needle assembly is in fluidic communication with both the primary compound and secondary compound.
3. Dial up/set a desired dose of the primary compound from the injection device, for example, via a graphical user interface (GUI).
4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.
5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.
6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The first and the second proximal needle of the injection device need to be permanently fixed to the dispense interface. Moreover they need to be fixed in such a way that the connection between the needle and the dispense interface in this case provides a tight connection as well. This fixation is especially problematic in medical devices, since any contamination of the drug agents with chemical substances must be avoided. The chemical substances can cause undesired side effects for the user if the drug agent comes into contact with it during the process of injection. This makes the use of adhesives problematic, because if the adhesive is used to tightly fix the connection between needle and dispense interface, a contamination of the guided drug agent can not be avoided.

Other means of fixation, for example purely mechanical means, often do not provide the necessary leak tightness.

Moreover it is necessary that the needle is fixed in both of its axial directions. Firstly, the needle needs to be fixed during the above mentioned step 1, such that the needle is able to pierce a reservoir. Secondly, the needle also needs to be fixed during a potential removal of the dispense interface from the injection device. The dispense interface needs to be exchanged due to hygienic reasons or because a drug is exchanged and a contamination of drug agents with other drug agents is strictly to be avoided.

Thus the invention faces the technical problem of providing a tight connection between a tube and a dispense interface, while at the same time the biocompatibility of the connection can be improved.

The technical problem is solved by an apparatus comprising a tube configured to guide a medium and a dispense interface. The tube comprises a first opening and a second opening, while the dispense interface comprises a recess. The recess has a first opening and a second opening and the tube is at least in part inserted into the recess. The tube is permanently affixed to the dispense interface by a combination of an interference fit and an adhesive, such that the interference fit prevents the adhesive from contaminating the medium.

By the combination of an interference fit with an adhesive it is possible to prevent the adhesive from contaminating the medium. This provides an improved biocompatibility for the connection of the tube and the dispense interface for the medical device. At the same time it is not necessary to dispense with an adhesive as an effective means for a permanent fixation. Hence, at the same time an effective permanent fixation can be provided without jeopardizing the biocompatibility.

The term inserting is understood to mean that the tube might be inserted either in part or completely, preferably from the first opening of the recess. In case the tube is in its axial direction longer than the recess, then, if the tube is inserted completely into the recess, still a part of the tube might protrude from the recess. It is also possible that the tube is protruding from the recess on both openings of the recess.

By the first opening and the second opening the recess in particular connects a first region with a second region. The first region can provide a reservoir containing a medicament, for example, and the second region can be a circular reservoir of a manifold or of a valve pocket. When the tube is inserted into the recess, the tube can especially provide a fluid connection between the reservoir in the first region and the circular reservoir of the manifold.

The interference fit can in particular also be utilized for a determination, how far the tube can be inserted into the channel. Since the tube might be pulled out from the recess the same way it was inserted, an interference fit often only provides a secure fixation in one axial direction. The adhesive thus has the function of a retaining adhesive permanently fixing the tube.

It is preferred when the tube is a needle or a cannula. It is especially useful to use needles or cannulas in an apparatus according to the invention, since a needle or cannula is frequently exposed to tensile and compression loads during injections and removals, so that it must be securely fixed. A needle or cannula is furthermore most of the time in direct contact with the guided medium, especially a drug agent or a medicament, and biocompatible connections are mandatory.

If the dispense interface is a dispense interface of a medical device and in particular of a drug delivery device, an improved biocompatibility can be provided for such a device, where biocompatibility is extremely important, since the medium, which is in most cases a drug agent or a medicament, must not be contaminated with substances, which might cause side effects for the user.

The dispense interface can in particular be a complete dispense interface or a part of a dispense interface, in particular an inner body of a dispense interface. Due to hygienic and medical reasons the dispense interface must be regularly exchanged, resulting in physical stress. The drug or medicament is guided through the dispense interface, in particular an inner body of the dispense interface. Thus parts of the dispense interface can be in direct contact with medium. Over the tube, in particular the needle or cannula, the dispense interface can be connected to a drug reservoir, for example. It is possible to provide a permanent fixation between the tube and the dispense interface and maintain the necessary biocompatibility for the guided medium.

It is especially preferred if the recess is at least in part gradually tapering. The recess tapers preferably from the first to the second opening of the recess. By an at least in part gradually tapering of the recess, an easy assembly of the tube and the dispense interface is provided since a centering or alignment during the insertion of the tube takes place. Moreover, the insertion force is evenly distributed and the growing force by the recess on the tube occurs gradually instead of all at once. This also reduces the total force necessary to insert the tube into the recess. Hence the insertion during the assembly process is made smoother and better controllable.

According to a further embodiment of the invention, the recess comprises a first section configured to accept an adhesive and the recess comprises a second section adjacent to the first section configured to provide the interference fit between the tube and the dispense interface. This way avoidance of the contamination of the guided medium can be realized particularly easily with a cost saving design. While the second section provides the interference fit, which is established first, the first section provides an area to accept the adhesive. This way the adhesive remains close to the tube and mostly in the recess. A contamination of other parts is therefore minimized. The section might be tapered, but a cylindrical geometry is possible as well, for example.

It is further preferred, if the second section tapers at least in part from the first section towards the second opening. This way an easy assembly, of the tube and the dispense interface is provided since a centering or alignment during the insertion of the tube takes place. Moreover the insertion force is evenly distributed and the growing force by the recess on the tube occurs gradually instead of all at once. This also reduces the total force necessary to insert the tube into the recess. Hence the insertion during the assembly process is made smoother and better controllable.

The first section can be tapered, cylindrical or exhibit any other suitable shape.

It is especially preferred, when the second section comprises a substantially cylindrical portion between the first section and the second opening. The cylindrical shape provides a very tight interference fit over a larger area. The cylindrical portion is preferably adjacent to the second opening of the recess.

It is further especially preferred, if the first section tapers from the first opening towards the second section, the second section in the area of the second opening is cylindrical and the second section tapers between the first section and the cylindrical portion. This way the cylindrical portion provides the interference fit, and the tapered first section and the tapered part of the second section are a guide for the insertion of the tube into the recess and likewise facilitate the insertion of the adhesive.

It is also possible though that the complete second section is designed cylindrical.

It is preferred, when the first section tapers at least in part from the first opening towards the second section. The tapering of the first section facilitates the acceptance of an adhesive. The tapering of the first section has preferably a larger angle to the axis of the recess than the tapering of the second recess. This way enough space for the acceptance of an adhesive is provided. Moreover the insertion and alignment of the tube is further facilitated.

According to another embodiment of the invention, the recess is tapered such that an interference fit is provided when the second opening of the tube is positioned in the region of the second opening of the recess. This way an optimum possible contact area between the inner wall of the recess and the outer wall of the tube is provided. The interference fit can in particular provide a security that tube is in right position. If one could move the tube further into the recess with a too low resistance, a certain uncertainty over position of the second opening of the tube in relation to the second opening of the recess.

According to another embodiment of the invention, the dispense interface is made from Cyclo Olefin Polymer (COP). COP is a biocompatible material and thus perfectly suitable for the dispense interface. This material can be used to mold the dispense interface, in particular the inner body of a dispense interface. By molding the dispense interface, complex structures can be easily produced. Especially the recess can directly be molded into the dispense interface.

Moreover, COP can be doped with a laser welding additive increasing the sensitivity to laser light. This way the dispense interface can be laser welded to further elements of the medical device.

It is further preferred when the tube, in particular the needle or cannula, is made from metal, in particular stainless steel. This material is shows a high degree of biocompatibility and provides the necessary rigidity, in particular for needles.

It is in particular possible to produce a connection between a tube and a dispense interface, wherein the tube comprises a first opening and a second opening, wherein the dispense interface comprises a recess, wherein the recess has a first opening and a second opening, by the steps of permanently affixing the tube to the dispense interface by inserting the tube at least in part into the recess and affixing the tube to the dispense interface by an interference fit and applying an adhesive in the region of the first opening of the recess.

Preferably the tube is inserted at least in part into the recess, wherein the tube is affixed to the dispense interface by an interference fit, before an adhesive in the region of the first opening of the recess is applied, which permanently affixes the tube to the dispense interface. This way a contamination of the medium can be completely avoided.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
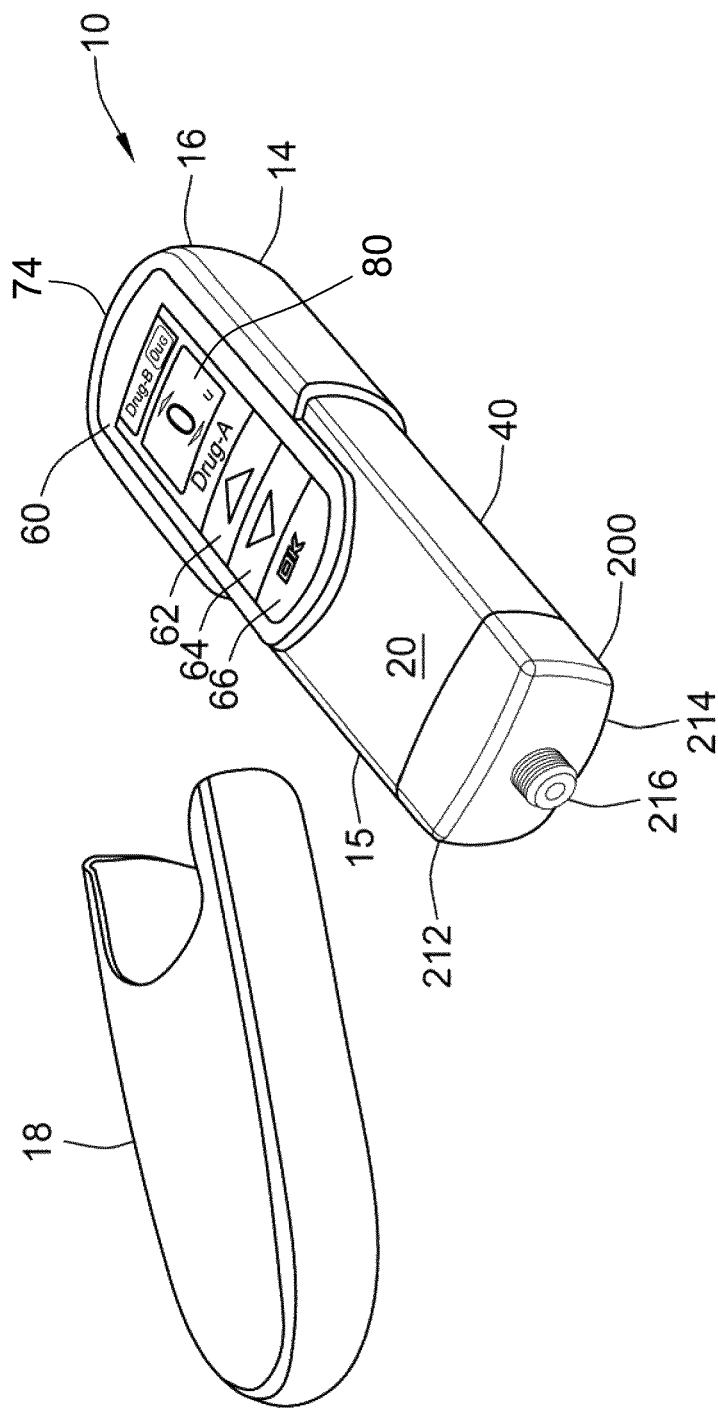
FIG. 1 illustrates a perspective view of a delivery device with an end cap of the device removed.
Figure 2:
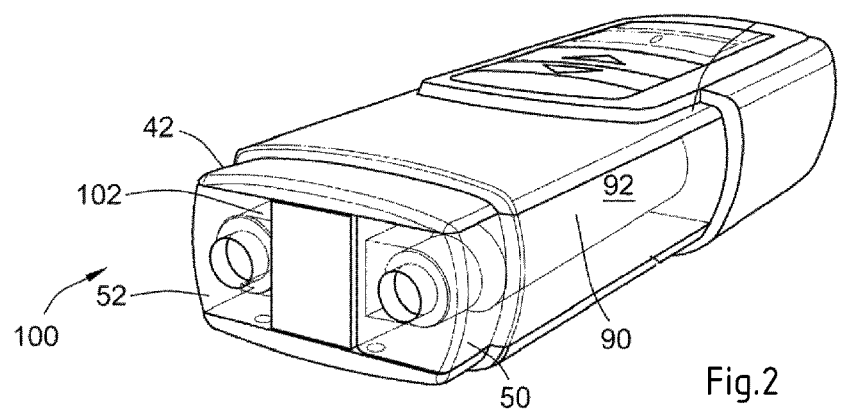
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
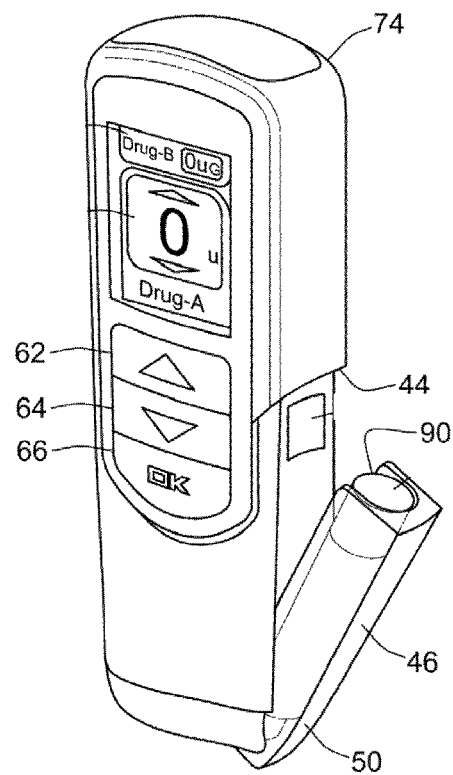
FIG. 3 illustrates a perspective view of the delivery device illustrated in FIG. 1 or 2 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
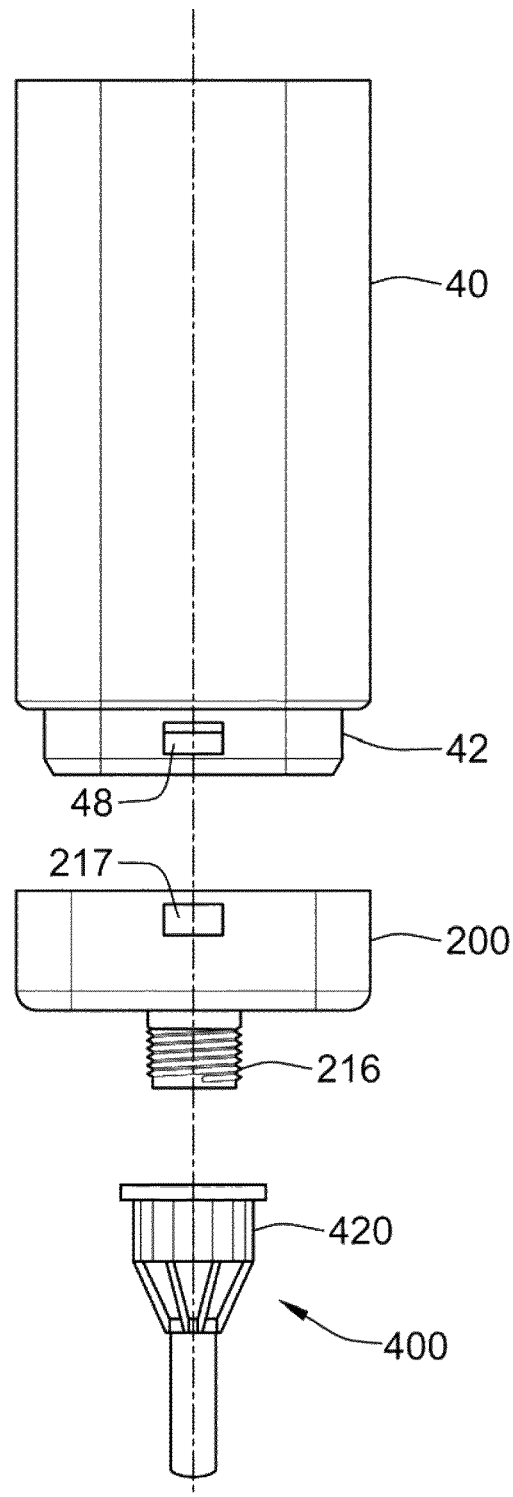
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
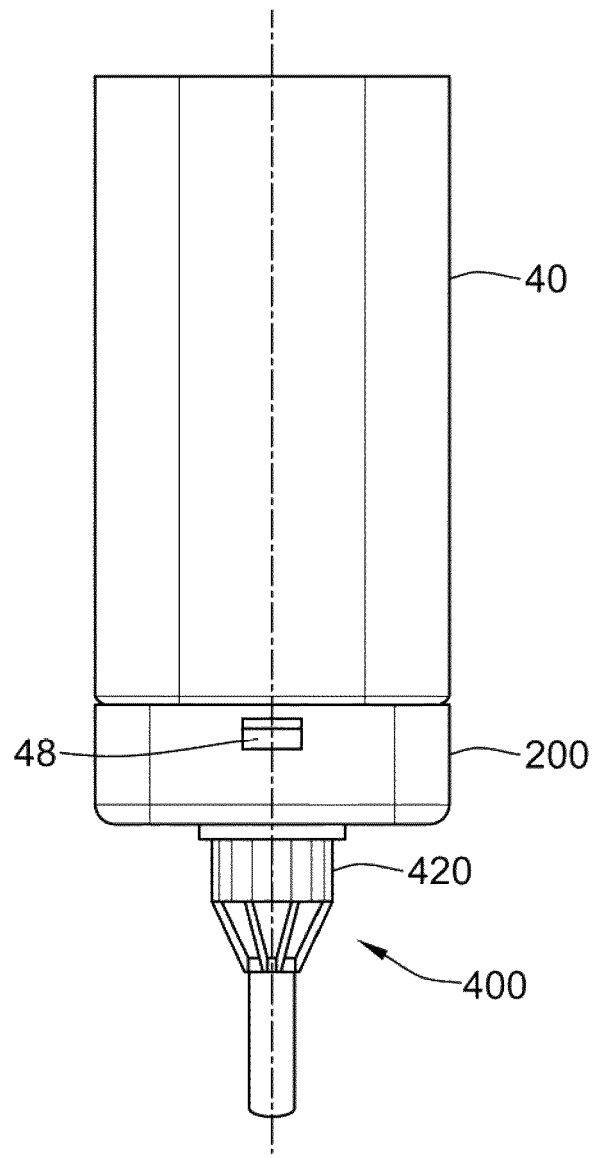
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
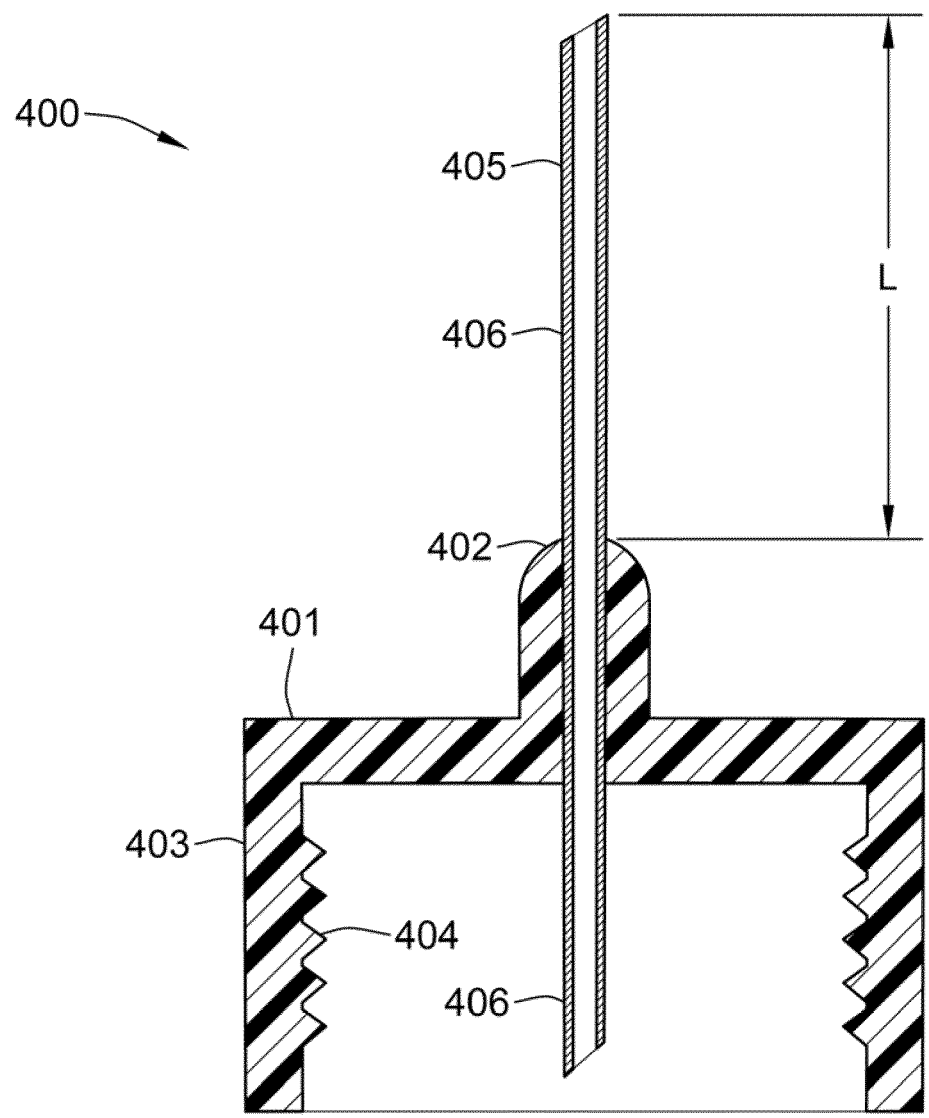
FIG. 6 illustrates one arrangement of a needle assembly that may be mounted on a distal end of the delivery device.
Figure 7:
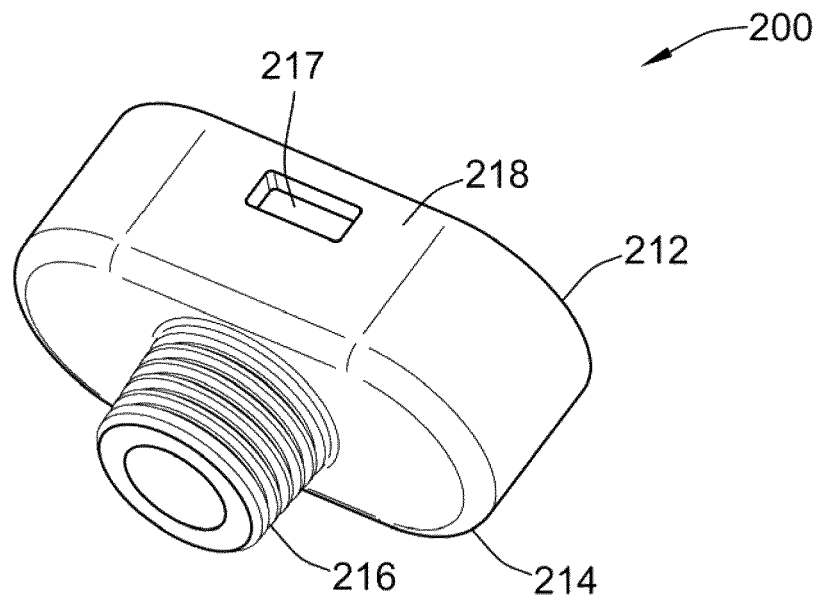
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
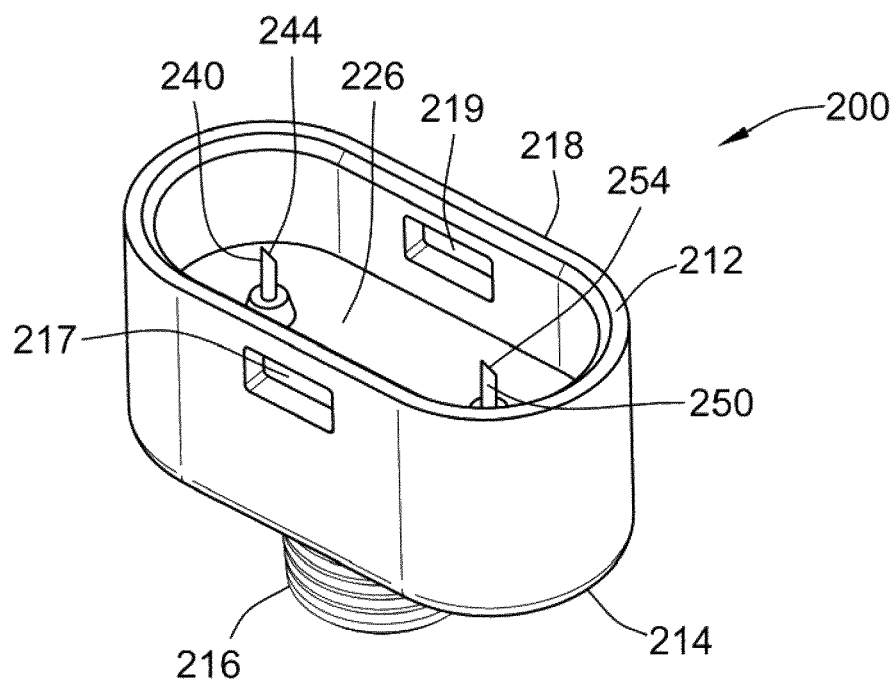
FIG. 8 illustrates another perspective view of the dispense interface illustrated in FIG. 4.
Figure 9:
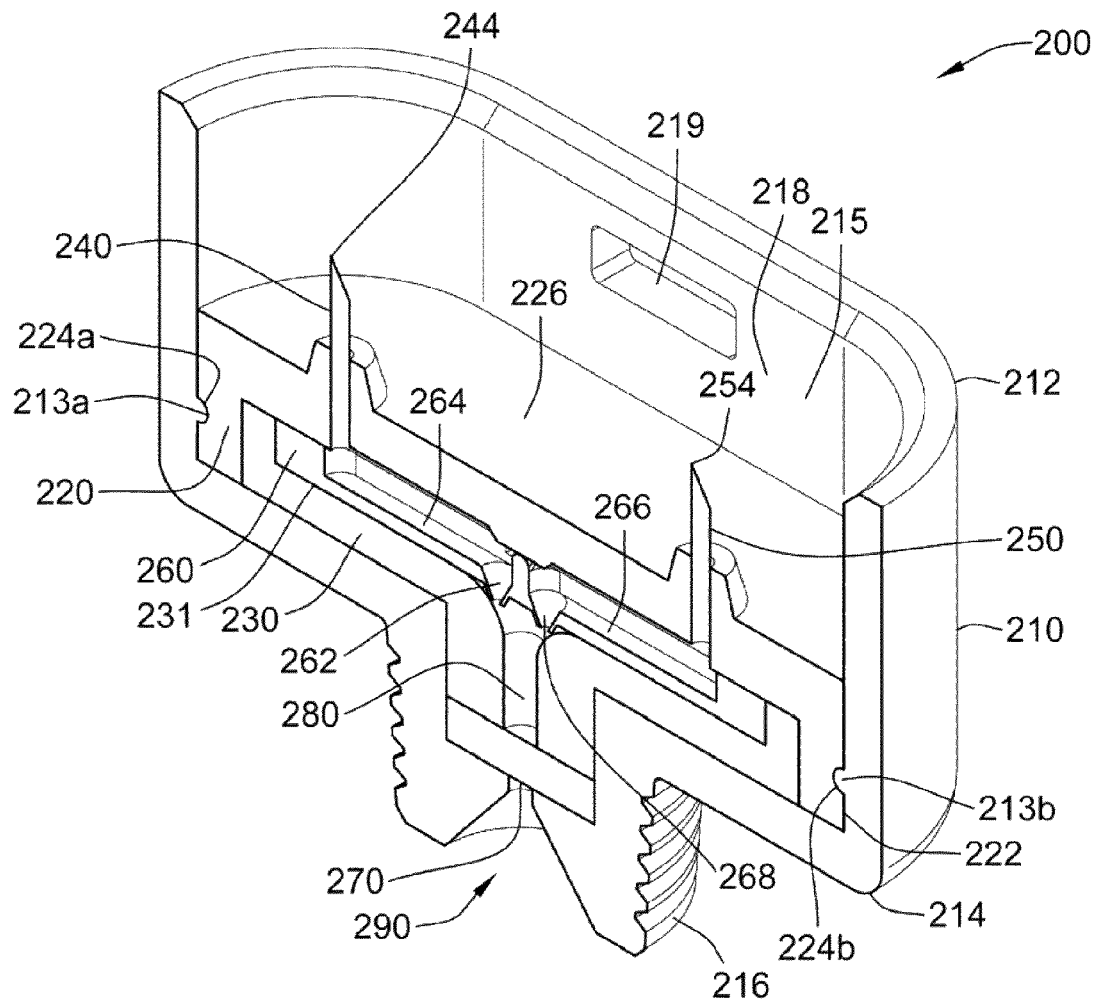
FIG. 9 illustrates a cross-sectional view of the dispense interface illustrated in FIG. 4.
Figure 10:
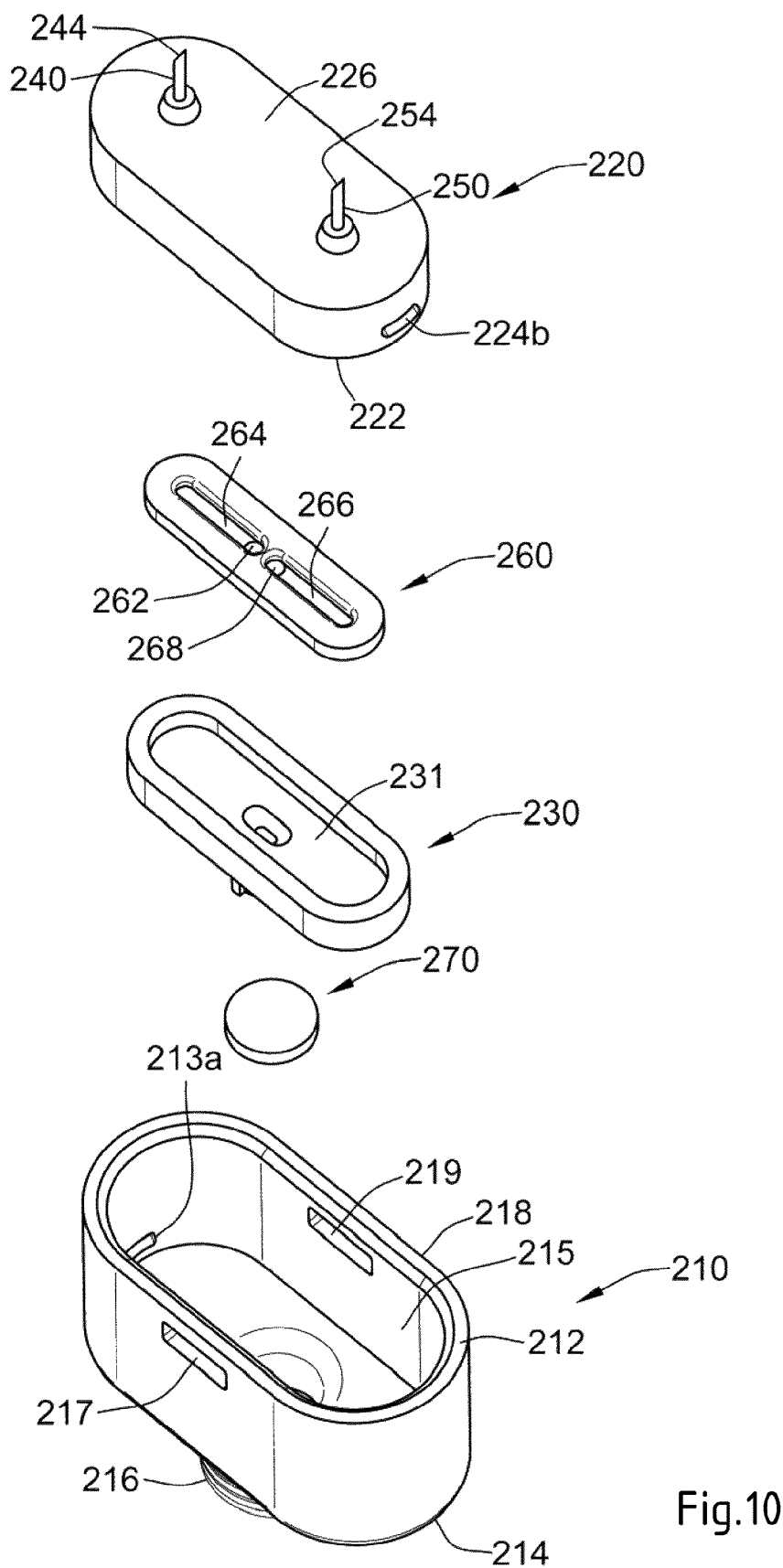
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
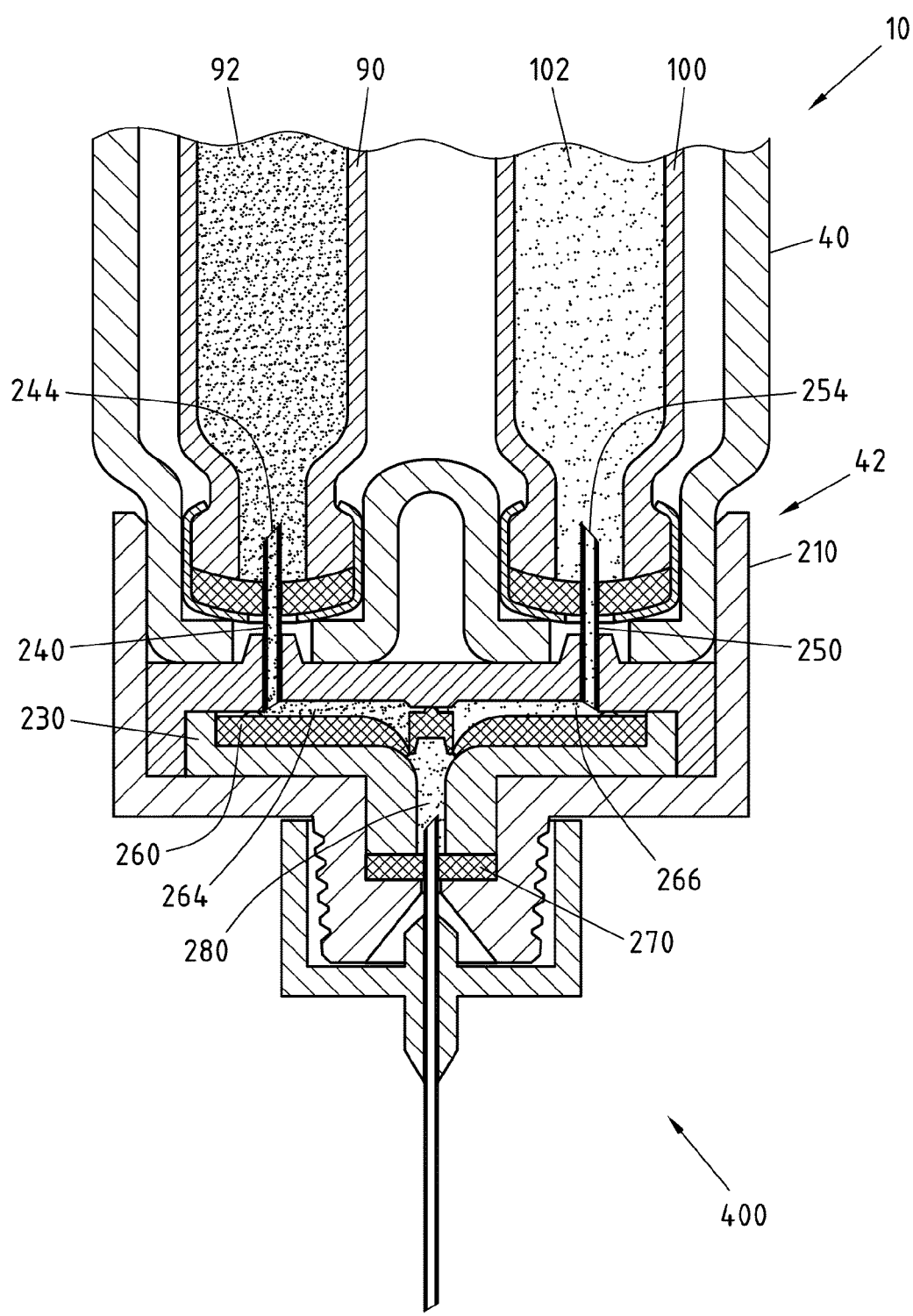
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
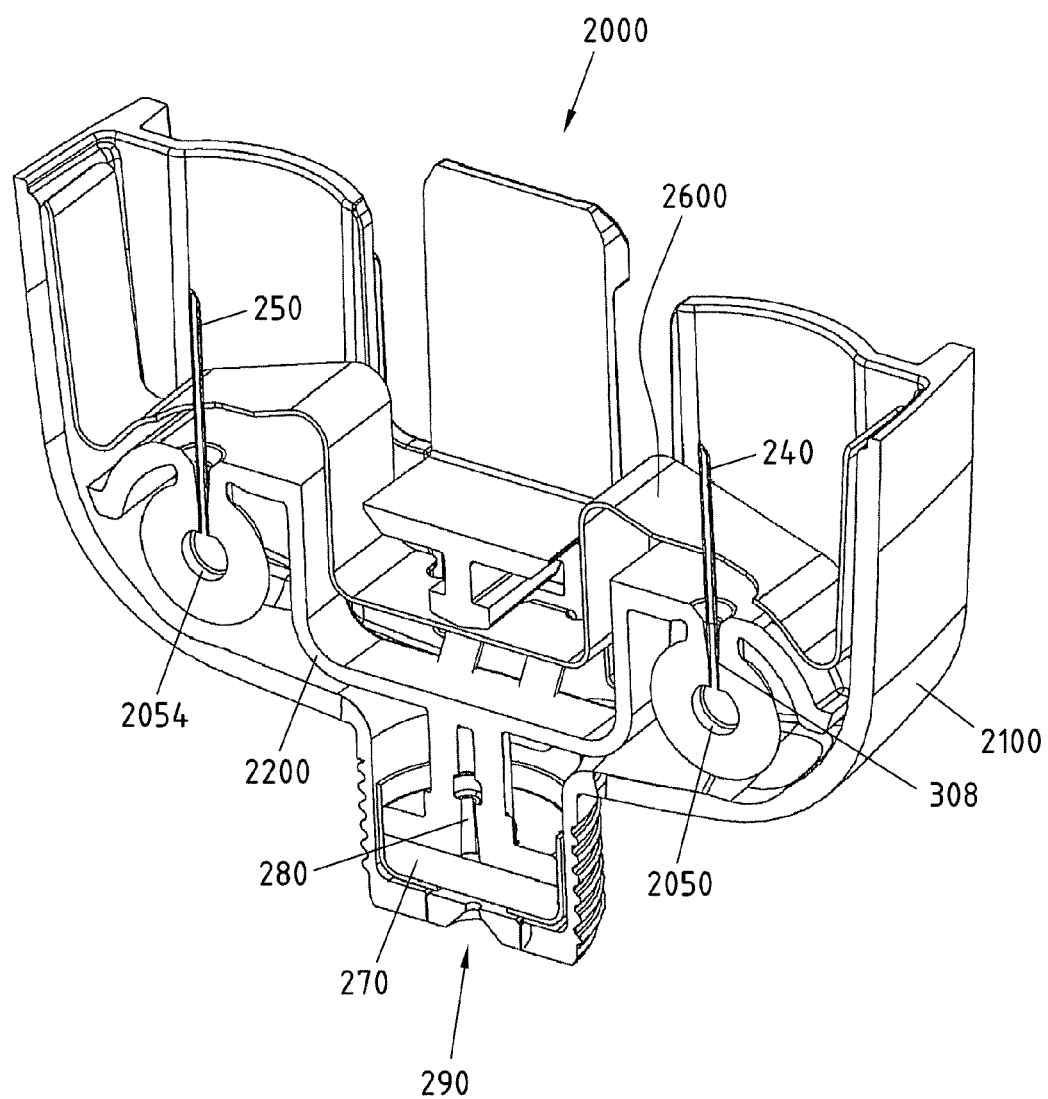
FIG. 12 illustrates a cross-sectional view of an alternative embodiment of a dispense interface.
Figure 13:
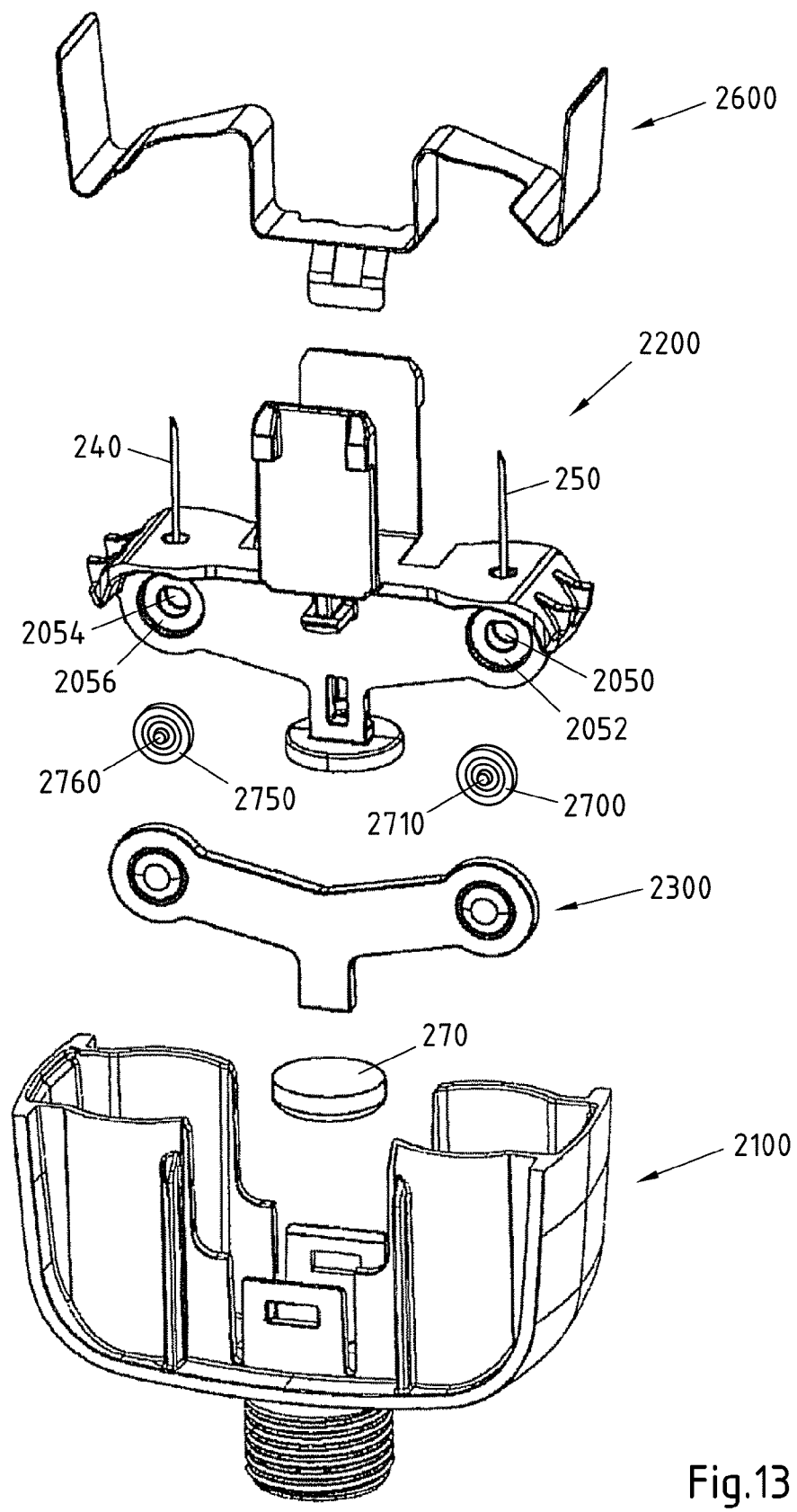
FIG. 13 illustrates an exploded view of the alternative embodiment of a dispense interface illustrated in FIG. 12.
Figure 14:
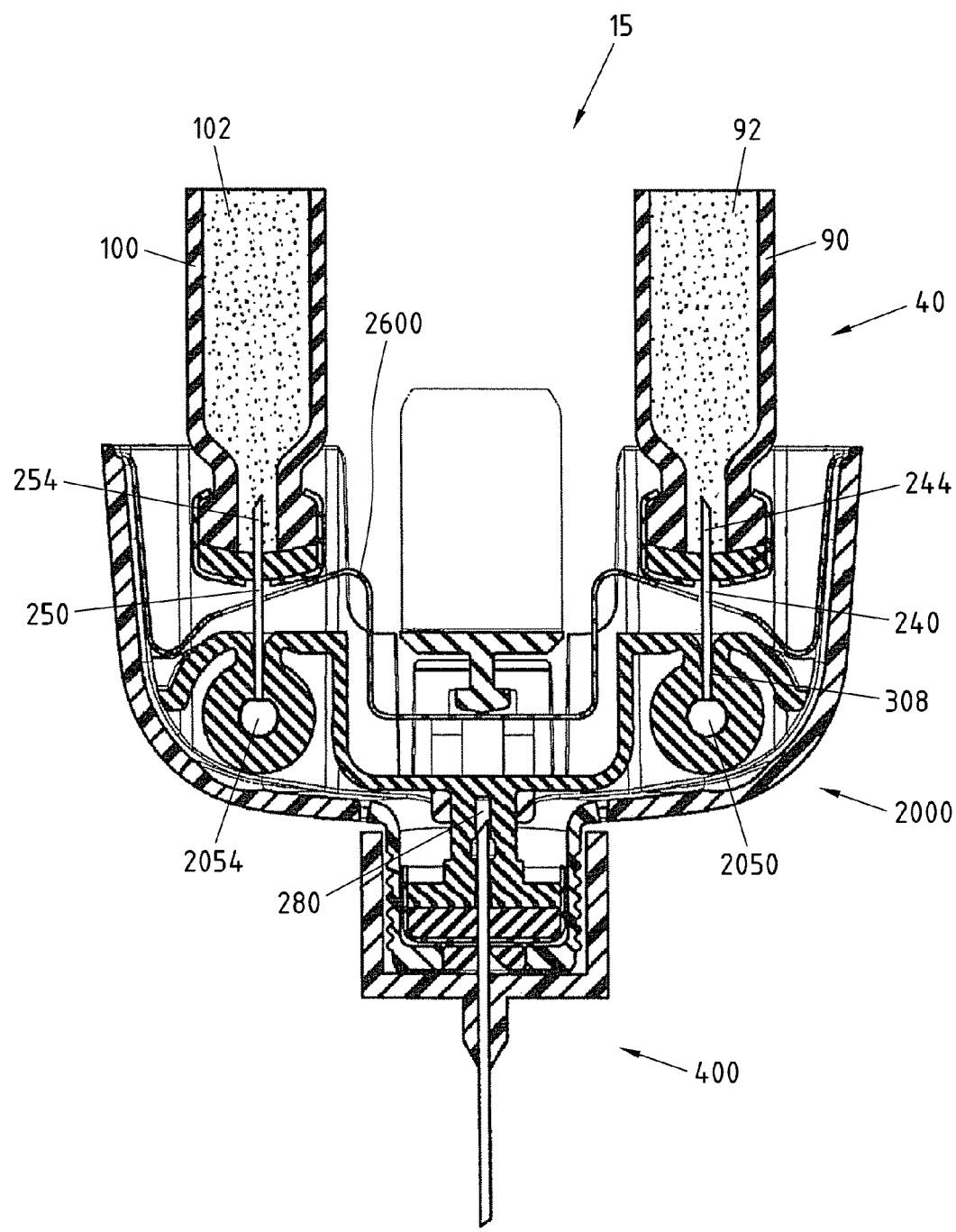
FIG. 14 illustrates a cross-sectional view of the alternative embodiment of a dispense interface illustrated in FIG. 12 and the dose dispenser mounted onto a drug delivery device, such as the device illustrated in FIG. 1.

FIGS. 12 to 14 illustrate an embodiment of a dispense interface 2000 alternative to the embodiment of the dispense interface 200 illustrated in FIGS. 7 to 11. In FIGS. 12 to 14 the same reference signs as in FIGS. 7 to 11 are used for the same parts. Furthermore, at this point, it is mainly referred to the above description of the embodiment of the dispense interface 200 illustrated in FIGS. 7 to 11 and, basically, the differences are described only.

One exemplary difference between the dispense interface 200 and the dispense interface 2000 is the outer shape. In particular, the dispense interface 2000 is attachable to a drug deliver device by axial attachment means as described above and at least partially insertable in the drug delivery device. For instance, once the dispense interface 2000 is attached to the distal end of the drug delivery device, the distal end of the main body of the drug delivery device covers a portion of the dispense interface 2000.

As will now be discussed in greater detail, in one preferred arrangement, the dispense interface 2000 illustrated in FIGS. 12 to 14 comprises:
  a. a main outer body 2100;
  b. an inner body 2200;
  c. a manifold 2300;
  d. a first piercing needle 240;
  e. a second piercing needle 250;
  f. a lock-out spring 2600;
  g. a first diaphragm valve (e.g. diaphragm 2700);
  h. a second diaphragm valve (e.g. diaphragm 2750); and
  i. an outer septum 270.

In FIG. 12 the main outer body 2100 comprises in particular an inner body 2200. The inner body 2200 comprises a first and a second piercing needle 240 and 250. The first piercing needle 240 is attached to the inner body 2200 and provides a fluid connection to a first circular reservoir 2050 of the inner body 2200. Likewise the second piercing needle 250 is attached to the inner body 2200 and provides a fluid connection to a second circular reservoir 2054 of the inner body 2200.

In the exploded view illustrated in FIG. 13, a more detailed view of the inner body 2200 is given. Moreover, a perspective view of both a first diaphragm 2700 and the second diaphragm 2750 are provided. The first and second diaphragms 2700 and 2750 correlate with the first and second reservoirs 2050 and 2054. As can be seen from these exploded views, the first diaphragm 2700 is substantially disc shaped and comprises a circular protrusion 2710 near the center of this disc shape. Similarly, the second diaphragm 2750 is substantially disc shaped and comprises a circular protrusion 2760 near the center of this disc shape. The diaphragm 2700 can provide a fluid seal between the first circular reservoir 2050 defined by the inner body 2000 and a fluid groove arrangement in the manifold 2300 (not shown). For instance, a rim of the diaphragm may be pressed on a set-back 2052 of the circular reservoir 2050 such that the diaphragm is in a pre-stressed state. Likewise, the diaphragm 2750 can provide a fluid seal between the second circular reservoir 2054 defined by the inner body 2000 and a fluid groove arrangement in the manifold 2300 (not shown). For instance, a rim of the diaphragm may be pressed on a set-back 2056 of the circular reservoir 2054 such that the diaphragm is in a pre-stressed state.

The manifold can in particular provide a y-channel which guides a fluid form the first and second circular reservoirs 2050 and 2054 into the holding chamber 280.

FIG. 14 illustrates the dispense interface 2000 after it has been mounted onto the distal end of the cartridge holder 40 of a drug delivery device such as the drug delivery device 10 illustrated in FIG. 1. As illustrated, the needle assembly 400 is mounted to the distal end of the dispense interface 2000. Fluid flow will now be explained with respect to FIG. 14.

As illustrated in FIG. 14, the dispense interface 2000 is coupled to the distal end of a cartridge holder 40. This cartridge holder 40 is illustrated as containing the first cartridge 90 containing the primary medicament 92 and the second cartridge 100 containing the secondary medicament 102. Once coupled to the cartridge holder 40, the dispense interface 2000 essentially provides a mechanism for providing a fluid communication path from the first and second cartridges 90, 100 to the holding chamber 280 defined by the inner body 2200. This holding chamber 280 is illustrated as being in fluid communication with the needle assembly 400 (i.e. the double ended needle assembly 400). As illustrated, the proximal needle of the double ended needle assembly 400 is in fluid communication with the holding chamber 280.

The proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with the first reservoir 2050 defined by the inner body 2000.

Similarly, the proximal piercing end 254 of the second piercing needle 250 resides in fluid communication with the secondary medicament 102 of the second cartridge 100. A distal end of the second piercing needle 250 will also be in fluid communication with the second circular reservoir 2054 defined by the inner body 2000.

For instance, as pressure builds up in the first cartridge 90 and the second cartridge 100, fluidic pressure will build up in both the first and second piercing needles 240, 250. As such, the pressure will be built up in both the first and second reservoirs 2050, 2054 and this fluidic pressure will invert the first and second diaphragms 2700, 2750. For instance, a fluidic pressure threshold has to be overcome to invert the first and second diaphragm valves.

This inversion of the first diaphragm 2700 will allow the first medicament 92 to flow out of the first reservoir 2050, around the now inverted first diaphragm 2700 and then into a fluid groove of the manifold 2300 (not shown). Similarly, this inversion of the second diaphragm 2750 will allow the second medicament 102 to flow out of the second reservoir 100, around the now inverted second diaphragm 2750 and then into a fluid groove of the manifold 2300. Under this continued pressure, the medicaments will then flow into the holding chamber 280 of the inner body 2200. Alternatively or additionally, the medicament may then flow out of the outlet 290 of the dispense interface 2000.

Figure 15A:
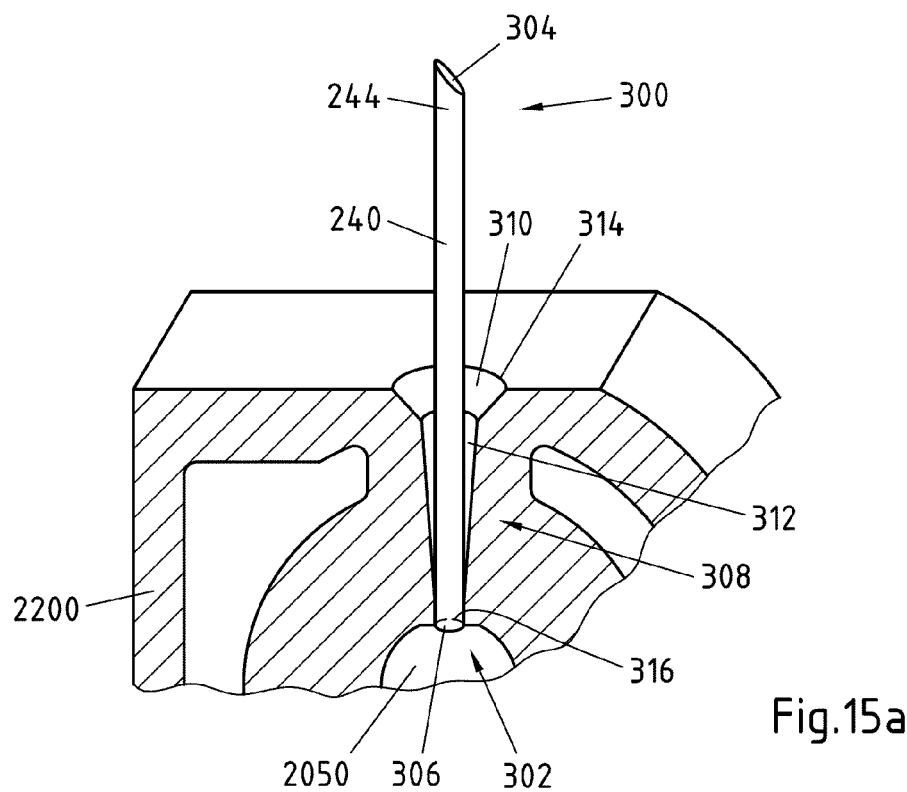
FIG. 15a illustrates an enlarged view of the first piercing needle and a part of the dispense interface illustrated in FIG. 12 without an adhesive.

FIG. 15a provides an enlarged view of the first piercing needle 240 together with the circular reservoir 2050 and a part of the inner body 2200. The description given with respect to FIGS. 15a and b applies likewise to the second piercing needle 250 together with the circular reservoir 2054.

Here, the tube is designed as a needle, in particular a piercing needle 240. The dispense interface, in this case, is the inner body 2200 of the dispense interface 2000. Though, the dispense interface can as well be the first inner body 220 illustrated in FIG. 10, for example. Here, the piercing needle 240 can guide a drug agent 92 from the reservoir 90, situated in a first region 300, into a second region 302, which is in this case the circular reservoir 2050. A drug agent 92 can enter the piercing needle 240 at the piercing end portion 244 through the first opening 304. The drug agent 92 can enter the circular reservoir 2050 through the second opening 306 of the needle 240.

The needle 240 is inserted into the recess 308. The recess 308 comprises a first section 310 and a second section 312. The first section 310 is tapered with a larger angle to the axial direction of the recess 308 or the needle 240 than the second region 312. The first region gradually tapers from the first opening 314 of the recess 308 towards the second region 312 and provides a volume to accept an adhesive 318. The second region 312 gradually tapers from the first region 310 towards the second opening 316 of the recess 308 and thus provides the interference fit for the needle 240. The second opening 306 of the needle 240 is substantially aligned with the second opening 316 of recess 308. It is as well possible that the tapering is provided in different geometric forms, departing from a gradual tapering. It is also possible to provide a recess 308, which provides an interference fit, without any tapering at all. Though, by the tapering of the recess 308 an easy assembly of the needle 240 and the inner body 2200 is provided since a centering or alignment during the insertion of the needle 240 takes place. Moreover the insertion force is evenly distributed and the growing force by the recess 308 on the needle 240 occurs gradually instead of all at once. This also reduces the total force necessary to insert the needle 240 into the recess 308. Hence the insertion during the assembly process is made smoother and better controllable. The state depicted in FIG. 15a is problematic in so far that the needle 240 might be pulled out of the recess 308 in the direction towards the first region 300 under certain circumstance, for example when the dispense interface 2000 is ejected from the cartridge holder 40.

Figure 15B:
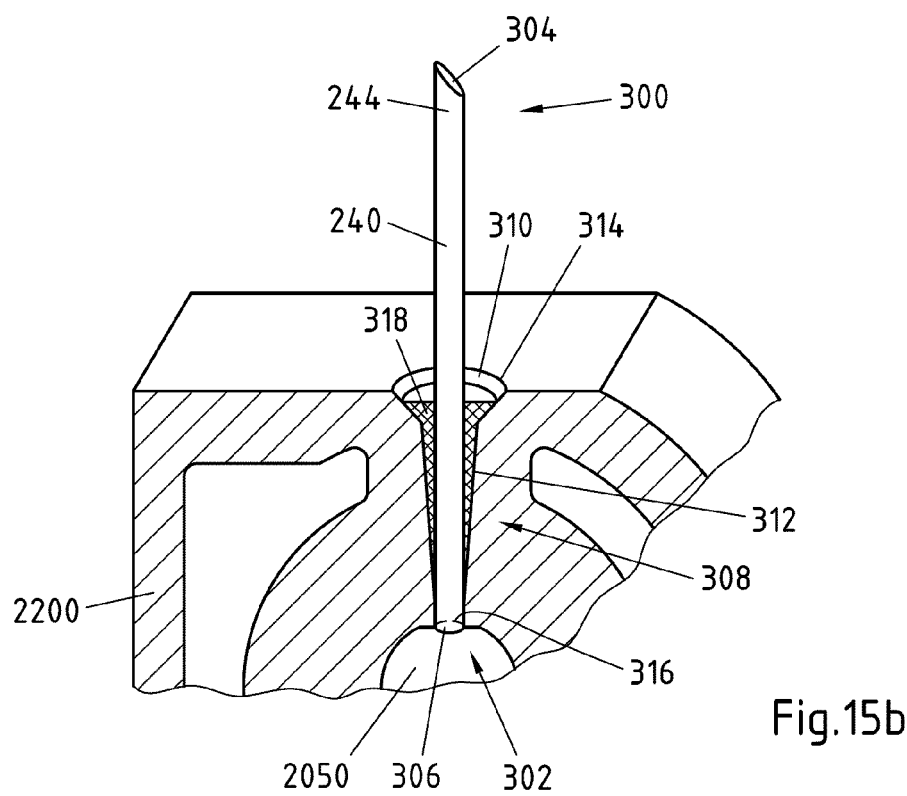
FIG. 15b illustrates the assembly illustrated in FIG. 15a with an adhesive provided in the recess.

Thus FIG. 15b shows the assembly illustrated in FIG. 15a with an adhesive 318 provided in the recess 308. Due to the interference fit the adhesive 318 cannot get into contact with the medicament 92. The interference fit prevents the adhesive 318 from flowing into the circular reservoir 2050. That means that even adhesives 318, which do not show a sufficient biocompatibility, may be used to fix the piercing needle 240 to the inner body 2200, because the medicament 92 does not get into contact with the adhesive 318.

As illustrated in FIG. 15b the adhesive 318 substantially fills the recess 308. Though, it is also possible that the adhesive 318 only fills a part of the recess 308, for example only the second section 308. It is also possible that the adhesive 318 substantially only fills the first section 310 of the recess 308 for example if in the second section 308 the piercing needle 240 is held by a press fit. The adhesive 318 may also protrude from the recess 308 into the first region 300. Since there is a fluid tight connection between the reservoir 90 and the needle 240, an adhesive protruding into the first region 300 does not contaminate any medicament 92. In this case it is important, that no adhesive 318 leaves the recess 308 through its second opening 316.

Figure 15C:
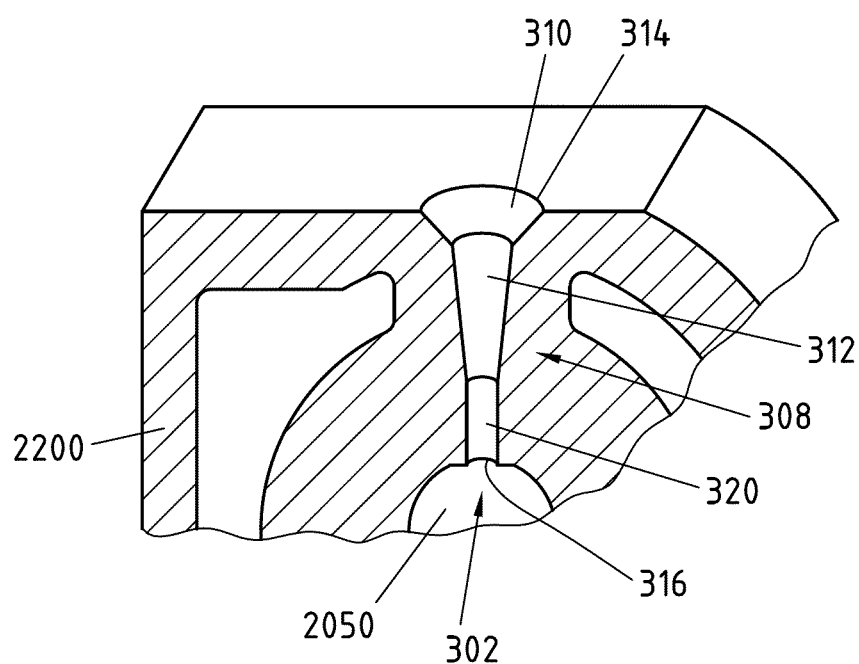
FIG. 15c illustrates another exemplary embodiment of a recess according to the invention.

FIG. 15c illustrates another exemplary embodiment of a recess 308 according to the invention. The difference to the embodiment shown in FIGS. 15a and 15b is the design of the second section 312. The second section 312 only tapers in part from the first section 310 towards the second opening 316. In the area of the second opening 316 the second section 312 has a substantially cylindrical portion 320. This cylindrical portion 320 provides the interference fit between the needle 240, 250 and the inner body 2200 of a dispense interface, while the tapered first section 310 and the tapered part of the second section 312 are a guide for the insertion of the needle 240, 250 into the recess 308 and also facilitate the insertion of the adhesive 318. The length of the tapered portion and the length of the substantially cylindrical portion 320 may vary. For example, the length of the cylindrical portion 320 may be 20 percent of the whole length of the second section 312 of the recess 308. In other embodiments, the length of the cylindrical portion may be 40, 50, 60, 70, or 80 percent of the second section 312 of the recess 308.

The needle 240 and the adhesive 318 can be inserted into the recess the same way as it is illustrated in FIGS. 15a and 15b.

The inner body 2200 may be made from Cyclo Olefin Polymer (COP), which is a biocompatible substance and which can be easily molded into the given geometric shape. Since a higher rigidity is needed for the piercing needle 240, it is preferably made from metal and in particular from steel. The needle 240 and the inner body 2200 can also be made from other materials, as long as a sufficient biocompatibility is guaranteed.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence

H His-Gly-Glu-Gly-Thr-Phe-Thr-Ser-Asp-Leu-Ser-Lys-Gln-Met-Glu-Glu-Glu-Ala-Val-Arg-

Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:
1. An apparatus comprising:
a first piercing needle and a second piercing needle,
each of the first piercing needle and the second piercing needle comprising a proximal piercing end and a distal end, and wherein each of the first piercing needle and the second piercing needle is configured to guide a medium, and
a dispense interface, comprising a mounting hub configured for releasable connection to a needle assembly,
wherein each of said first piercing needle and said second piercing needle comprises a first opening and a second opening,
wherein said dispense interface comprises a first recess and a second recess
wherein said first recess has a first opening and said second recess has a second opening,
wherein said distal end of said first piercing needle is at least partially inserted into said first recess, and said distal end of said second piercing needle is at least partially inserted into said second recess,
wherein said first piercing needle and said second piercing needle are permanently affixed to said dispense interface by a combination of an interference fit and an adhesive, such that said interference fit prevents said adhesive from contaminating said medium,
wherein said first recess and second recess each comprise a first section configured to accept said adhesive,
wherein said first recess and said second recess each comprise a second section adjacent to said first section configured to provide said interference fit between said first piercing needle and said second piercing needle respectively and said dispense interface,
wherein said second section comprises a tapered section and a substantially cylindrical portion between said first section and said second opening,
wherein said substantially cylindrical portion provides said interference fit,
and
wherein said dispense interface is configured to attach to a distal end of a reservoir holder comprising a first reservoir and a second reservoir such that the proximal piercing end of said first needle pierces the first reservoir and such that the proximal piercing end of said second needle pierces the second reservoir.

2. The apparatus according to claim 1, wherein said first piercing needle and said second piercing needle each are a needle or a cannula.

3. The apparatus according to claim 1, wherein said dispense interface is configured to attach to a medical device comprising a first cartridge of primary medicament and a second cartridge of secondary medicament.

4. The apparatus according to claim 1, wherein said first recess and said second recess are each at least in part gradually tapering.

5. The apparatus according to claim 1, wherein said second section tapers at least in part from said first section towards said second opening.

6. The apparatus according to claim 1, wherein said first section tapers at least in part from said first opening towards said second section.

7. The apparatus according to claim 1, wherein each recess is tapered such that said interference fit is provided when said second opening of said piercing needle is positioned in a region of said second opening of said recess.

8. The apparatus according to claim 1, wherein said inner body is made from Cyclo Olefin Polymer (COP).

9. The apparatus according to claim 1, wherein each piercing needle is made from metal.

* * * * *